US012409108B2

(12) United States Patent
Masanelli et al.

(10) Patent No.: US 12,409,108 B2
(45) Date of Patent: Sep. 9, 2025

(54) SOLID COSMETIC COMPOSITION CONTAINING AQUEOUS SPHEROIDS DISPERSED IN A SOLID CONTINUOUS ANHYDROUS PHASE

(71) Applicant: LVMH RECHERCHE, Saint Jean de Braye (FR)

(72) Inventors: Armelle Masanelli, Tigy (FR); Marlène Parcollet, Saint Jean de Braye (FR); Valérie De La Poterie, Lailly en Val (FR)

(73) Assignee: LVMH RECHERCHE, Saint Jean de Braye (FR)

( * ) Notice: Subject to any disclaimer, the term of this patent is extended or adjusted under 35 U.S.C. 154(b) by 740 days.

(21) Appl. No.: 17/418,139

(22) PCT Filed: Dec. 23, 2019

(86) PCT No.: PCT/FR2019/053285
§ 371 (c)(1),
(2) Date: Jun. 24, 2021

(87) PCT Pub. No.: WO2020/141274
PCT Pub. Date: Jul. 9, 2020

(65) Prior Publication Data
US 2022/0096335 A1 Mar. 31, 2022

(30) Foreign Application Priority Data
Dec. 31, 2018 (FR) ...................................... 1874417

(51) Int. Cl.
*A61K 8/02* (2006.01)
*A61K 8/04* (2006.01)
*A61K 8/25* (2006.01)
*A61K 8/31* (2006.01)
*A61K 8/34* (2006.01)
*A61K 8/37* (2006.01)
*A61K 8/42* (2006.01)
*A61K 8/60* (2006.01)
*A61K 8/81* (2006.01)
*A61K 8/88* (2006.01)
*A61K 8/92* (2006.01)
*A61Q 1/06* (2006.01)
*A61Q 1/12* (2006.01)
*A61Q 17/04* (2006.01)

(52) U.S. Cl.
CPC ............ *A61K 8/0229* (2013.01); *A61K 8/042* (2013.01); *A61K 8/25* (2013.01); *A61K 8/31* (2013.01); *A61K 8/342* (2013.01); *A61K 8/37* (2013.01); *A61K 8/42* (2013.01); *A61K 8/60* (2013.01); *A61K 8/8111* (2013.01); *A61K 8/88* (2013.01); *A61K 8/922* (2013.01); *A61K 8/927* (2013.01); *A61Q 1/06* (2013.01); *A61Q 1/12* (2013.01); *A61Q 17/04* (2013.01); *A61K 2800/33* (2013.01); *A61K 2800/43* (2013.01); *A61K 2800/522* (2013.01); *A61K 2800/524* (2013.01); *A61K 2800/591* (2013.01); *A61K 2800/805* (2013.01)

(58) Field of Classification Search
CPC ........ A61K 8/0229; A61K 8/042; A61K 8/25; A61K 8/31; A61K 8/342; A61K 8/37; A61K 8/42; A61K 8/60; A61K 8/8111; A61K 8/88; A61K 8/922; A61K 8/927; A61K 2800/33; A61K 2800/43; A61K 2800/522; A61K 2800/524; A61K 2800/591; A61K 2800/805; A61K 8/0216; A61K 8/064; A61K 8/345; A61K 8/86; A61K 8/89; A61K 8/92; A61Q 1/06; A61Q 1/12; A61Q 17/04; A61Q 1/02; A61Q 19/00
See application file for complete search history.

(56) References Cited

U.S. PATENT DOCUMENTS 7,244,419 B2   7/2007  Yamato et al.
2002/0159961 A1  10/2002  Yamato et al.
2003/0165451 A1   9/2003  Lennon et al.
(Continued)

FOREIGN PATENT DOCUMENTS

EP     2617409 A1   7/2013
EP     2979690 B1   8/2021
(Continued)

OTHER PUBLICATIONS

International Search Report and Written Opinion issued for International Patent Application No. PCT/FR2019/053285, Date of mailing: Apr. 21, 2020, 12 pages including English translation of Search Report.

(Continued)

*Primary Examiner* — Robert A Wax
*Assistant Examiner* — Andre Mach
(74) *Attorney, Agent, or Firm* — HSML P.C.

(57) ABSTRACT

The invention relates to a solid cosmetic composition comprising aqueous spheroids dispersed in a solid anhydrous continuous phase. The invention is also directed toward a process for preparing a solid cosmetic composition according to the invention, and also a process for making up and/or caring for bodily and/or facial skin using a solid cosmetic composition according to the invention. The invention is also directed toward a stick or a solid gel cast in a dish or a pot, and more particularly a lipstick, a foundation, and an antisun stick, comprising a cosmetic composition according to the invention.

25 Claims, No Drawings

(56) References Cited

U.S. PATENT DOCUMENTS

| | | |
|---|---|---|
| 2004/0229984 A1 | 11/2004 | Yamato et al. |
| 2007/0237732 A1 | 10/2007 | Yamato et al. |
| 2013/0142853 A1 | 6/2013 | Matsuo et al. |
| 2015/0004111 A1 | 1/2015 | Lahousse |
| 2021/0077362 A1* | 3/2021 | Rehault .................... A61K 8/37 |

FOREIGN PATENT DOCUMENTS

| | | | |
|---|---|---|---|
| FR | 2820739 | 8/2002 | |
| FR | 2922104 A1 * | 4/2009 | ............. A61K 8/732 |
| FR | 2985180 | 7/2013 | |
| JP | 2007022950 | 2/2007 | |
| JP | 2012062289 A | 3/2012 | |
| WO | 2013102570 | 7/2013 | |
| WO | 2018115328 | 6/2018 | |
| WO | 2018167309 | 9/2018 | |

OTHER PUBLICATIONS

Search Report issued for French Patent Application No. 1874417, dated Sep. 24, 2019, 2 pages.

* cited by examiner

SOLID COSMETIC COMPOSITION CONTAINING AQUEOUS SPHEROIDS DISPERSED IN A SOLID CONTINUOUS ANHYDROUS PHASE

TECHNICAL FIELD

The invention relates to a solid cosmetic composition comprising aqueous-phase spheroids dispersed in a solid anhydrous continuous phase. The invention also relates to a process for preparing a solid cosmetic composition according to the invention. The invention is also directed toward the use of a solid cosmetic composition according to the invention for making up and/or caring for bodily and/or facial skin. Finally, the invention relates to a process for making up and/or caring for bodily and/or facial skin using a solid cosmetic composition according to the invention.

PRIOR ART

The cosmetics industry is, as ever, in search of compositions which produce surprising effects. These may be compositions which have a novel visual appearance, for example by dispersing solid particles of various colors in a transparent continuous phase. They may also be novel compositions combining performance qualities that are difficult to associate via conventional techniques, such as freshness and gloss, freshness and persistence, or gloss and persistence.

Cosmetic compositions comprising beads dispersed in a fluid continuous phase already exist.

EP 2 979 690 describes, for example, a process for preparing round beads comprising an aqueous phase in an emulsion of the water-in-oil or oil-in-water type, coated at the surface with a solid material for better stabilization over time. However, said process does not allow the manufacture of solid aqueous beads.

WO 2018/167309 proposes cosmetic compositions comprising a silica-based fatty phase and an aqueous phase in the form of beads, obtained by means of a microfluidic process. The drops consist of a shell, gelled by polymerization, and of a liquid core.

There are to date no solid cosmetic compositions stably combining two immiscible phases, one being dispersed in the other. The reason for this is that such solid compositions comprising aqueous spheroids without an outer coating cannot be prepared via the processes described in the prior art since the incorporation of aqueous spheroids into a hot liquid anhydrous continuous phase by stirring would damage them by making them partly coalesce or by deforming them. The processes of the prior art do not make it possible either to adjust the size of the beads, which depends either on the stirring or on the weight and gravity. Thus, a first problem underlying the invention consists in obtaining a cosmetic composition that is solid at room temperature, consisting of a solid anhydrous continuous phase comprising dispersed aqueous spheroids, in which the aqueous spheroids are suspended and stabilized, do not become deformed, and do not leach materials into the solid anhydrous continuous phase.

In addition, the provision of cosmetic compositions that look attractive and have a pleasant and surprising feel during application to the skin remains an ongoing objective. A second problem underlying the invention consists in obtaining a composition in which the aqueous spheroids and the solid anhydrous continuous phase in which they are dispersed are flexible enough to be readily crushed and applied to the skin, and thus in combining the properties of the two phases.

A third problem underlying the invention is that of obtaining a cosmetic composition whose texture is rigid enough for it to be able to be prepared in various forms, for example in the form of a stick or cast in a dish or a pot, and which is supple enough for it to be able to be taken up by rubbing or by means of a sponge and applied comfortably to the skin.

Last but by no means least, a final problem underlying the invention consists in obtaining a macroscopically heterogeneous cosmetic composition that is particularly stable and non-allergenic, which has better persistence and better tolerance on the skin due to the absence of surfactants.

DESCRIPTION OF THE INVENTION

According to a first aspect, the present invention is directed toward a cosmetic composition that is solid at room temperature, comprising:
 aqueous spheroids comprising at least one hydrophilic gelling agent and water, said spheroids being dispersed in
 an anhydrous continuous phase, which is solid at room temperature, comprising at least one hydrocarbon-based oil and/or one silicone oil and at least one lipophilic structuring agent.

The surfactant content in the solid cosmetic composition of the invention is preferably less than 4%, preferentially less than 3%, more preferentially less than 2%, and even more preferentially less than 1%, by weight relative to the total weight of said composition. The solid cosmetic composition of the invention is even more advantageously free of surfactant.

Unexpectedly, the inventors have observed that it is possible to prepare a solid cosmetic composition comprising two visually distinct phases. The solid cosmetic composition of the invention is a macroscopically heterogeneous product, which distinguishes it from macroscopically homogeneous emulsions (homogeneous mixture) obtained when a surfactant is used. The absence of surfactant in the solid cosmetic composition of the invention makes it particularly tolerant, and also enables its persistence to be improved. In addition, the presence of aqueous spheroids, which are visible to the naked eye, suspended in the anhydrous continuous phase makes the composition visually attractive. This effect is further enhanced by the fact that the aqueous spheroids can be colored.

Another advantage of the solid cosmetic composition of the invention is associated with its very easy application and its surprising texture at the moment of application to the skin. The aqueous spheroids and the solid anhydrous continuous phase which are immiscible mix together during the application to enhance a sensation of freshness on the surface of the skin, while at the same time combining the advantages of an anhydrous phase (nutrition, persistence, protection, etc.). Each of the two phases affords different properties, thus making it possible to obtain conflicting performance qualities that are usually difficult to associate, such as freshness and gloss, freshness and persistence, freshness and sun protection, etc. The surprising freshness sensory effect linked to the presence of aqueous spheroids is more pronounced than with conventional emulsions. For an identical water content, the solid cosmetic composition of the invention affords a much more pronounced freshness effect than an identical composition in emulsion form, in which the freshness effect is attenuated.

The cosmetic composition of the invention may also be prepared according to a process which enables packaging of the cosmetic composition as soon as it exits the process, without an additional step. The process of the invention is thus readily industrializable.

The aqueous spheroids and the solid anhydrous continuous phase are "immiscible", which means that the spheroids of the invention do not diffuse and do not disintegrate in the solid anhydrous continuous phase in which they are dispersed. Advantageously, the spheroids and the anhydrous continuous phase are immiscible when the two phases are in liquid form, and notably when they are heated to a temperature of greater than or equal to 40° C.

For the purposes of the invention, the cosmetic composition is considered as being solid when it does not become deformed or does not flow under its own weight. Thus, a gloss is not a solid cosmetic composition within the meaning of the invention. The solid cosmetic composition of the invention is considered as being solid when the anhydrous continuous phase and the aqueous spheroids have a hardness as defined according to the present invention.

For the purposes of the invention, the term "spheroid" targets a small solid of essentially spherical shape having the same composition throughout the spheroid. The spheroids of the invention have a sufficiently flexible and deformable texture, at room temperature, to be able to be applied easily to the skin by means of a small shear, for example with the fingers, and thus to produce a care or makeup effect on the skin. The diameter of the spheroids may range from 0.05 to 10.0 mm, preferably from 0.1 to 3.0 mm, and more preferentially from 0.5 to 2.5 mm, this diameter being a mean diameter measured on 10 measurements via conventional methods, for example using binocular magnifying glasses. These spheroids preferably have a regular appearance, a smooth surface and a uniform volume. Advantageously, the spheroids of the invention are free of any outer coating.

For the purposes of the invention, the term "room temperature" means a temperature of between 20 and 25° C.

In the context of the invention, the term "anhydrous" means that the water content of the object under consideration is preferably less than 1% by weight, and even more preferentially less than 0.5% by weight of said object. Thus, the term "anhydrous continuous phase" means that the continuous phase has a water content of less than or equal to 1% and preferably less than or equal to 0.5% by weight of said phase.

The anhydrous continuous phase advantageously has a dropping point of greater than 50° C., preferably ranging from 55 to 100° C., and more preferentially ranging from 60 to 80° C. For the purposes of the invention, the term "dropping point" means the temperature at which the anhydrous continuous phase passes from the solid state to the liquid state. The dropping point is determined according to the standard ASTM-D 3954.

For the purposes of the invention, the anhydrous continuous phase is considered as being solid when it has a hardness defined by a compression strength of greater than or equal to 50 g at 20° C., preferably greater than or equal to 80 g at 20° C., after penetration of a cylindrical spindle 5 mm in diameter into said phase to a depth of 10 mm at a speed of 1 mm·s$^{-1}$. Advantageously, when the cosmetic composition is in stick form, the anhydrous continuous phase has a hardness defined by the compression strength of greater than or equal to 80 g at 20° C. The hardness of the anhydrous continuous phase is preferentially defined by a compression strength of less than or equal to 2500 g at 20° C.

The solid anhydrous continuous phase makes it possible to keep the spheroids in suspension over a prolonged period of time, preferably greater than 1 month, more preferentially greater than 3 months and even more preferentially greater than 6 months. This structure gives the cosmetic composition of the invention a novel look, and also makes it possible to prevent and to limit the coalescence of the spheroids with each other. The anhydrous continuous phase also has suspending power at elevated temperature with respect to the spheroids, so that they remain suspended in the anhydrous continuous phase throughout the cooling phase.

In the solid cosmetic composition of the invention, the aqueous spheroids advantageously represent from 10% to 80%, more advantageously from 20% to 70% and even more advantageously from 30% to 60% by weight relative to the total weight of the solid cosmetic composition.

The aqueous spheroids advantageously have a hardness defined by a compression strength of greater than or equal to 20 g at 20° C., preferably greater than or equal to 30 g at 20° C. and even more preferentially greater than or equal to 40 g at 20° C., after penetration of a cylindrical spindle 5 mm in diameter into said phase to a depth of 10 mm at a speed of 1 mm·s$^{-1}$. The hardness of the aqueous spheroids is preferentially defined by a compression strength of less than or equal to 600 g, more preferentially less than or equal to 550 g and even more preferentially less than or equal to 500 g at 20° C., after penetration of a cylindrical spindle 5 mm in diameter into said phase to a depth of 10 mm at a speed of 1 mm·s$^{-1}$.

The inventors have observed that the nature of the constituents of the aqueous spheroids may have an influence not only on the ease of application of the cosmetic composition of the invention, but also on its final properties.

Hydrophilic Gelling Agent:

The content of hydrophilic gelling agent in the aqueous spheroids is advantageously at least 0.3%, more advantageously at least 0.5%, and even more advantageously at least 0.7%, by weight relative to the weight of the aqueous spheroids.

Hydrophilic gelling agents that may advantageously be mentioned include natural or synthetic polysaccharides, preferably chosen from agar-agar (such as Ina Agar CS 83 sold by Iwase Cosfa), gellan gum (such as Kelcogel® CG-LA sold by Azelis), xanthan gum (such as Rhodicare® T sold by Solvay Novecare or Keltrol CG LAX-T sold by CP Keltro), carrageenans (such as Satiagum™ VPC 430 sold by Cargill Beauty), cellulose and derivatives thereof such as hydroxyethylcellulose (such as Klucel® GF sold by Ashland) and hydroxypropylcellulose, corn starch, cellulose carboxymethyl ethers (such as Blanose™ 7H3SF sold by Ashland), copolymers based on bis-decyltetradeceth-20 ether (such as Adeka Nol GT-700 sold by Adeka), *alcaligenes* polysaccharides (such as Alcasealan sold by Iwase Cosfa), and mixtures thereof.

According to a particularly advantageous embodiment, the hydrophilic gelling agent of the invention is a natural polysaccharide preferably chosen from agar-agar, gellan gum, xanthan gum and mixtures thereof.

The solid cosmetic composition of the invention comprises at least agar-agar; this is the most preferred natural or synthetic polysaccharide.

The solid cosmetic composition of the invention advantageously comprises at least gellan gum; this is the most preferred natural or synthetic polysaccharide after agar-agar.

The solid cosmetic composition of the invention advantageously comprises at least xanthan gum; this is the most preferred natural or synthetic polysaccharide after agar-agar and gellan gum, respectively.

The amount of hydrophilic gelling agent present in the aqueous spheroids depends on the nature of the hydrophilic gelling agent, and is determined so that the aqueous spheroids have a hardness defined by a compression strength of greater than or equal to 20 g at 20° C., preferably greater than or equal to 30 g at 20° C., and even more preferentially greater than or equal to 40 g at 20° C., after penetration of a cylindrical spindle 5 mm in diameter into said phase to a depth of 10 mm at a speed of 1 mm·s$^{-1}$.

The aqueous spheroids may also comprise at least one glycol preferably chosen from polyglycols such as pentylene glycol, butylene glycol, glycerol, polyethylene glycols, and mixtures thereof. According to a particularly preferred embodiment, the glycol is vegetable glycerol. The glycol, and more particularly vegetable glycerol, aids the dispersion of the pigments and/or nacres in the composition, without it being necessary to add additional dispersants. This is an advantage over conventional alcohols, such as ethanol, the use of which requires the addition of additional dispersants to disperse any pigments and/or nacres. In addition, conventional alcohols, such as ethanol, cannot be used at high temperatures due to their low boiling point. Thus, the solid cosmetic composition of the invention may be free of alcohol, and more particularly of ethanol.

The glycol content in the aqueous spheroids advantageously ranges from 0 to 70%, preferably from 1% to 50%, and even more preferentially from 2% to 30%, by weight relative to the total weight of the aqueous spheroids.

The inventors have observed that the nature of the constituents of the anhydrous continuous phase may also have an influence not only on the ease of application of the cosmetic composition of the invention, but also on its final properties.

Hydrocarbon-Based Oils and/or Silicone Oils:

The hydrocarbon-based oil(s) and/or the silicone oil(s) may be present in a content ranging from 5% to 99.5% by weight, preferably from 10% to 95% by weight, more preferentially from 20% to 90%, even more preferentially from 30% to 85% by weight, and even more preferentially from 40% to 80% by weight, relative to the total weight of the anhydrous continuous phase.

The hydrocarbon-based oil(s) and/or the silicone oil(s) are chosen so as to be immiscible with the aqueous spheroids.

The hydrocarbon-based oil constituting the anhydrous continuous phase may be chosen from volatile hydrocarbon-based oils and/or nonvolatile hydrocarbon-based oils. It is preferably a mixture of hydrocarbon-based oils.

For the purposes of the invention, the term "hydrocarbon-based oil" means an oil mainly containing carbon and hydrogen atoms, and possibly oxygen, nitrogen, sulfur or phosphorus atoms.

For the purposes of the invention, a volatile hydrocarbon-based oil is an oil that is capable of evaporating on contact with the skin in less than one hour, at room temperature and atmospheric pressure. The volatile hydrocarbon-based oil(s) of the invention are oils that are liquid at room temperature, having a nonzero vapor pressure, at room temperature and atmospheric pressure, ranging in particular from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg). The term "nonvolatile hydrocarbon-based oil" means an oil that remains on the skin at room temperature and atmospheric pressure for at least several hours and that notably has a vapor pressure of less than 0.13 Pa ($10^{-3}$ mmHg).

The volatile hydrocarbon-based oils of the invention are advantageously chosen from hydrocarbon-based oils comprising from 8 to 16 carbon atoms, and notably branched alkanes comprising from 8 to 16 carbon atoms, for instance isoalkanes comprising from 8 to 16 carbon atoms (also known as isoparaffins) of petroleum origin, for instance isododecane (also known as 2,2,4,4,6-pentamethylheptane), isodecane and isohexadecane, for example the oils sold under the trade names Isopar™ or Permethyl (ExxonMobil Chemical), branched esters comprising from 8 to 16 carbon atoms, for instance isohexyl neopentanoate, and mixtures thereof. Other volatile hydrocarbon-based oils, for instance petroleum distillates, notably those sold under the name Shell Solt by the company Shell, may also be used. The volatile hydrocarbon-based oils may also be chosen from linear alkanes comprising from 8 to 16 carbon atoms. Examples of linear alkanes comprising from 8 to 16 carbon atoms that may be mentioned include n-nonadecane ($C_9$), n-decane ($C_{10}$), n-undecane ($C_{11}$), n-dodecane ($C_{12}$), n-tridecane ($C_{13}$), n-tetradecane ($C_{14}$), n-pentadecane ($C_{15}$) and n-hexadecane ($C_{16}$), and mixtures thereof, and in particular the mixture of n-undecane ($C_{11}$) and of n-tridecane ($C_{13}$) sold under the reference Cetiol UT by the company Cognis. According to one embodiment, a volatile linear alkane that is suitable for use in the invention may be chosen from n-nonadecane, n-undecane, n-dodecane and n-tridecane, and mixtures thereof.

The volatile hydrocarbon-based oils of the invention are advantageously chosen from volatile hydrocarbon-based oils comprising from 8 to 16 carbon atoms, and mixtures thereof.

Nonvolatile hydrocarbon-based oils that may notably be mentioned include: hydrocarbon-based oils of plant origin such as fatty acid triesters of glycerol, the fatty acids of which comprise from 4 to 24 carbon atoms, these oils possibly being linear or branched, and saturated or unsaturated. These oils are advantageously wheat germ oil, sunflower oil, grapeseed oil, sesameseed oil, corn oil, apricot oil, castor oil, shea oil, avocado oil, olive oil, soybean oil, sweet almond oil, palm oil, rapeseed oil, cottonseed oil, hazelnut oil, *macadamia* oil, jojoba oil, alfalfa oil, poppyseed oil, pumpkin oil, marrow oil, blackcurrant oil, evening primrose oil, millet oil, barley oil, *quinoa* oil, rye oil, safflower oil, candlenut oil, passionflower oil or musk rose oil; or alternatively caprylic/capric acid triglycerides, for instance those sold by the company Stéarinerie Dubois or those sold under the names Miglyol® 810, 812, 818, 829 and 840 by the company Dynamit Nobel; or alternatively linear or branched hydrocarbons, comprising from 4 to 24 carbon atoms, of mineral or synthetic origin, such as petroleum jelly, polydecenes, hydrogenated polyisobutene such as Parleam®, squalane, and mixtures thereof; synthetic esters, for instance Purcellin™ oil (cetostearyl octanoate), isopropyl myristate, isopropyl palmitate, benzoates of an alcohol comprising from 12 to 15 carbon atoms, hexyl laurate, diisopropyl adipate, isononyl isononanoate, 2-ethylhexyl palmitate, isostearyl isostearate, octanoates, decanoates or ricinoleates of alcohols or of polyalcohols, for instance propylene glycol dioctanoate; hydroxylated esters, for instance isostearyl lactate, diisostearyl malate; pentaerythritol esters; fatty alcohols that are liquid at room temperature, bearing a branched and/or unsaturated carbon-based chain comprising from 12 to 26 carbon atoms, for instance octyldodecanol, isostearyl alcohol, oleyl alcohol, 2-hexyldecanol, 2-butyloctanol or 2-undecylpentadecanol; higher fatty acids such as oleic acid, linoleic acid or linolenic acid; carbonates; acetals; citrates; and mixtures thereof.

The nonvolatile hydrocarbon-based oils of the invention are advantageously chosen from fatty acid triesters of glycerol, the fatty acids of which comprise from 4 to 24 carbon atoms, linear or branched hydrocarbons, comprising from 4 to 24 carbon atoms, of mineral or synthetic origin, fatty alcohols that are liquid at room temperature, bearing a branched and/or unsaturated carbon-based chain comprising from 12 to 26 carbon atoms, hydroxylated esters and synthetic esters. The hydrocarbon-based nonvolatile oils of the invention may be advantageously chosen from polyglyceryl-2 triisostearate, octyldodecanol, hydrogenated polyisobutene, polydecenes and isononyl isononanoate.

The silicone oil constituting the anhydrous continuous phase may be chosen from volatile silicone oils and/or nonvolatile silicone oils. It is preferably a mixture of silicone oils.

Volatile silicone oils that may be mentioned include volatile silicones, for instance volatile linear or cyclic silicone oils, notably containing from 2 to 7 silicon atoms, these silicones optionally including at least one alkyl or alkoxy group comprising from 1 to 10 carbon atoms. Preferred volatile silicone oils that may be mentioned include cyclopentadimethylsiloxane, octamethylcyclotetrasiloxane, decamethylcyclopentasiloxane, dodecamethylcyclohexasiloxane, hepta methylhexyltrisiloxane, hepta methyloctyltrisiloxane, hexa methyldisiloxane, octamethyltrisiloxane, decamethyltetrasiloxane and dodecamethylpentasiloxane, and mixtures thereof.

Mention may also be made of volatile linear alkyltrisiloxane oils chosen from 3-butyl-1,1,1,3,5,5,5-heptamethyltrisiloxane, 3-propyl-1,1,1,3,5,5,5-heptamethyltrisiloxane and 3-ethyl-1,1,1,3,5,5,5-heptamethyltrisiloxane, and mixtures thereof.

The preferred volatile silicone oil is cyclopentadimethylsiloxane.

Nonvolatile silicone oils that may be mentioned include polydimethylsiloxanes (PDMS) including at least one alkyl or alkoxy group advantageously comprising from 12 to 24 carbon atoms, which are on the side and/or at the end of the silicone chain, phenyl silicones, for instance phenyl trimethicones, phenyl dimethicones, phenyltrimethylsiloxydiphenylsiloxanes, diphenyl dimethicones, di phenyl methyldiphenyltrisiloxanes and 2-phenylethyl trimethylsiloxysilicates.

Mention may also be made of fluoro oils chosen from fluorosilicone oils, fluoropolyethers and fluorosilicones. Nonafluoromethoxybutane and perfluoromethylcyclopentane are among the preferred fluoro oils.

The hydrocarbon-based oil(s) and/or the silicone oil(s) constituting the anhydrous continuous phase are combined with at least one lipophilic structuring agent.

Lipophilic Structuring Agent:

The lipophilic structuring agent constituting the anhydrous continuous phase of the invention may be chosen from waxes, butters, pasty fatty compounds and/or lipophilic gelling agents, and preferably lipophilic gelling agents.

The content of lipophilic structuring agent may range from 0.5% to 95% by weight, preferably from 1% to 90% by weight, preferentially from 3% to 90% by weight, more preferentially from 3% to 60%, even more preferentially from 4% to 45% by weight and even more preferentially from 5% to 30% by weight relative to the total weight of the anhydrous continuous phase.

The wax(es) used in the context of the invention may be lipophilic compounds, which are solid at room temperature, with a reversible solid/liquid change of state, having a melting point of greater than 30° C., preferably from 40 to 120° C., more preferentially from 50 to 110° C. and even more preferentially from 60 to 100° C. For the purposes of the invention, the melting point corresponds to the temperature of the most endothermic peak observed on thermal analysis (DSC), as described in the standard NF EN ISO 11357-3. The melting point of the wax may be measured using a differential scanning calorimeter (DSC), for example the calorimeter sold under the name Modulated DSC 2920 by the company TA Instruments.

Mixtures of waxes may advantageously be formed by combining waxes with a high melting point, i.e. with a melting point of greater than 50° C., preferably greater than 70° C., with waxes having lower melting points, i.e. with a melting point of less than 50° C., preferably less than or equal to 40° C. The mixing of waxes with a high melting point with waxes with a low melting point should make it possible to obtain an anhydrous continuous phase having a dropping point of greater than 50° C.

The wax(es) used in the context of the invention may be chosen from waxes that are solid at room temperature, of animal, plant, mineral or synthetic origin, and mixtures thereof.

Advantageously, the wax(es) of the invention may be chosen from:

hydrocarbon-based waxes, for instance beeswax, lanolin wax, Chinese insect waxes, rice bran wax, carnauba wax, candelilla wax, ouricury wax, esparto grass wax, cork fiber wax, sugar cane wax, olive wax, berry wax, shellac wax, Japan wax, sumach wax, montan wax, orange and lemon waxes, paraffins and ozokerite;
 waxes of fatty alcohols chosen from linear or branched, saturated or unsaturated fatty alcohols comprising from 20 to 60 carbon atoms, such as the stearyl heptanoate-stearate caprylate mixture (PCL Solid from Symrise);
 silicone waxes, for instance alkyl or alkoxy dimethicones comprising from 16 to 45 carbon atoms;
 fluoro waxes;
 hydrocarbon waxes advantageously comprising from 18 to 60 carbon atoms, such as Microcrystalline Wax SP-88 and Microcrystalline Wax SP-16 W (Strahl and Pitsch Inc.) and polyethylene waxes such as the waxes Jeenate® (Jeen International Corporation) and Performalene® (Baker Hughes); and
 mixtures thereof.

According to one variant of the invention, the wax(es) of the invention are a mixture of natural waxes, of hydrocarbon-based waxes, of fatty alcohol waxes comprising from 20 to 60 carbon atoms, the hydrocarbon waxes comprising from 18 to 60 carbon atoms. The wax(es) of the invention may be advantageously chosen from beeswax, rice bran wax, polyethylene waxes, carnauba wax, candelilla wax and the stearyl heptanoate-stearate caprylate mixture.

According to a preferred embodiment, the butter(s) may be chosen from C10-18 triglycerides (INCI name: C10-18 Triglycerides) including at room temperature and at atmospheric pressure a liquid fraction and a solid fraction, shea butter, Karité nilotica (*Butyrospermum parkii*) butter, galam (*Butyrospermum parkii*) butter, Borneo butter or grease or tengkawang (*Shorea stenoptera*) tallow, *shorea* butter, illipé butter, *madhuca* or *Bassia madhuca longifolia* butter, mowrah (*Madhuca latifolia*) butter, katiau (*Madhuca mottleyana*) butter, phulwara (*M. butyracea*) butter, mango (*Mangifera indica*) butter, *murumuru* (*Astrocatyum murumuru*) butter, kokum (*Garcinia indica*) butter, ucuuba (*Virola sebifera*) butter, tucuma butter, painya (Kpangnan) (*Pentadesma butyracea*) butter, coffee (*Coffea arabica*) butter, apricot (*Prunus armeniaca*) butter, macadamia (*Macadamia temifolia*) butter, grape (*Vitis vinifera*) seed butter, avocado (*Persea gratissima*) butter, olive (*Olea europaea*) butter, sweet almond (*Prunus amygdalus dulcis*) butter, cocoa (*Theobroma cacao*) butter, sunflower butter, the butter under the INCI name *Astrocaryum murumuru* Seed Butter, the butter under the INCI name *Theobroma grandiflorum* Seed Butter, the butter under the INCI name *Irvingia gabonensis* Kernel Butter, jojoba esters (mixture of hydrogenated jojoba wax and oil) (INCI name: Jojoba Esters), ethyl esters of shea butter (INCI name: Shea butter ethyl esters), and mixtures thereof. The most preferred butters are shea, cupuaçu, cocoa, avocado and mango butter.

The term "pasty fatty compound" denotes a noncrystalline fatty compound including, at room temperature and atmospheric pressure, a liquid fraction and a solid fraction. The pasty compound is chosen, for example, from the group consisting of lanolin and derivatives thereof, such as C10-30 cholesterol/lanosterol esters, polymeric silicone compounds, copolymers of alkyl (meth)acrylates preferably containing a C8-C30 alkyl group, homopolymer and copolymer oligomers of vinyl esters containing C8-C30 alkyl groups, homopolymer and copolymer oligomers of vinyl ethers containing C8-C30 alkyl groups, liposoluble polyethers resulting from polyetherification between one or more C2-050 diols, copolymers of ethylene oxide and/or of propylene oxide with C6-C30 long-chain alkylene oxides, diglycerol esters, arachidyl propionate, phytosterol esters, noncrosslinked polyesters resulting from polycondensation between a linear or branched C4-C50 dicarboxylic or polycarboxylic acid and a diol or a polyol, the ester resulting from the esterification reaction of hydrogenated castor oil with isostearic acid such as a monoisostearate, diisostearate or triisostearate of hydrogenated castor oil, a mixture of soybean sterols and of oxyethylenated (5 OE) oxypropylenated (5 OP) pentaerythritol, and mixtures thereof.

Lipophilic gelling agents that may advantageously be mentioned include clays, optionally modified hectorites, dextrin esters, polyamides or silicone polyamides, L-glutamic acid or aspartic acid amides, hydroxystearic acid, and hydrocarbon-based block copolymers comprising at least one styrene unit, and preferably optionally modified hectorites, dextrin esters, polyamides or silicone polyamides, L-glutamic acid or aspartic acid amides and hydrocarbon-based block copolymers comprising at least one styrene unit. According to a preferred embodiment, the lipophilic gelling agent is chosen from dibutyl lauroyl glutamide and dibutyl ethylhexanoyl glutamide, polyamide-8 resin, dextrin palmitate, dextrin myristate, glyceryl behenate/eicosadioate, copolymers based on castor oil and caprylic/capric triglycerides, and mixtures thereof.

It should be noted that when hydroxystearic acid is used as lipophilic gelling agent, it is always used in combination with another lipophilic gelling agent.

The hectorites may be hectorites modified with a quaternary alkylammonium chloride, preferably an ammonium substituted with at least one and preferably at least two alkyl groups comprising from 14 to 20 carbon atoms. The alkyl may advantageously be stearyl. Mention will be made of the compound having the INCI name Disteardimonium Hectorite, in which the ammonium comprises two methyl groups and two stearyl groups.

For the purposes of the invention, the dextrin esters are esters of dextrin and of a fatty acid comprising from 12 to 24 carbon atoms, preferably comprising from 14 to 22 carbon atoms, and even more preferentially comprising from 14 to 18 carbon atoms. Preferably, the dextrin esters are chosen from dextrin myristate, dextrin palmitate, and mixtures thereof.

The amides of L-glutamic acid (glutamides) or of aspartic acid preferably comprise at least one alkanoyl group comprising from 6 to 14 carbon atoms, for example 8 or 12 carbon atoms. Such a glutamic acid amide is described, for example, in patent FR 2 820 739. The glutamides are preferably chosen from dibutyl lauroyl glutamide, dibutyl ethylhexanoyl glutamide, and mixtures thereof, and may be, for example, one of the products having the brand names EB-21, GP-1, AJK-OD2046, AJK-BG2055 and AJK-CE2046, manufactured by the company Ajinomoto. The glutamide is chosen, for example, from dibutyl lauroyl glutamide and dibutyl ethylhexanoyl glutamide, or mixtures thereof.

The amide or the mixture of amides, notably of glutamide(s), represents, for example, between 0.1% and 15.0%, between 0.5% and 15.0%, between 1.0% and 8.0%, between 1.0% and 5.0%, or even between 2.0% and 5.0%, by weight relative to the total weight of the anhydrous continuous phase.

For the purposes of the invention, the hydrocarbon-based block copolymers comprising at least one styrene unit are preferably block copolymers of styrene and of an olefin, for instance copolymers comprising at least one styrene unit and a unit chosen from butadiene, ethylene, propylene, butylene, isoprene, and mixtures thereof. The hydrocarbon-based block copolymers of the invention are advantageously chosen from styrene-ethylene/propylene copolymers, styrene-ethylene/propylene-styrene copolymers, styrene ethylene/butadiene-styrene copolymers, styrene-isoprene-styrene copolymers, styrene-butadiene-styrene copolymers, styrene-ethylene/butylene-styrene copolymers, styrene/methylstyrene/indene copolymers, and mixtures thereof.

The preferred lipophilic gelling agents are chosen from dibutyl lauroyl glutamide (such as AJK OD2046 sold by Ajinomoto), dibutyl ethylhexanoyl glutamide (such as AJK GP-1 sold by Ajinomoto), polyamide-8 resin (such as SP OleoCraft™ LP20 sold by Croda), dextrin palmitate (such as Rheopearl KL2 sold by Miyoshi), dextrin myristate (such as Rheopearl MKL2 sold by Miyoshi), glyceryl behenate/eicosadioate (such as Nomcort sold by SACI-CFPA), disteardimonium hectorite (such as Bentone® 38 V CG sold by SACI-CFPA), copolymers based on castor oil and caprylic/capric triglycerides (such as Estogel M sold by DKSH), and mixtures thereof.

According to an advantageous embodiment, the anhydrous continuous phase of the cosmetic composition of the invention is free of silica.

The cosmetic composition of the invention may also comprise, either in the aqueous spheroids or in the anhydrous continuous phase, or in both, and preferably in the spheroids, at least one pigment and/or one nacre, and preferably at least one organic or inorganic pigment. The pigment and/or the nacre may have been surface-treated, i.e. they may have undergone one or more surface treatments of chemical, electronic, mechanochemical and/or mechanical nature.

The content of pigment and/or nacre advantageously ranges from 0 to 40% by weight, and preferably from 2% to 10% by weight, relative to the total weight of the solid cosmetic composition.

The cosmetic composition of the invention may also comprise, either in the aqueous spheroids or in the anhydrous continuous phase, or in both, at least one UV-screening agent.

When it is present in the anhydrous continuous phase, the UV-screening agent is advantageously chosen from benzophenone-3, ethylhexyl salicylate, octocrylene, octyl methoxycinna mate, homosalate, polysilicone-15, diethylamino hydroxybenzoyl hexyl benzoate, bis-ethylhexyloxyphenol methoxyphenyl triazine, titanium oxide or zinc oxide pigments, and mixtures thereof.

When it is present in the aqueous spheroids, the UV-screening agent is advantageously phenylbenzimidazolesulfonic acid, benzophenone-4, or a nanotitanium or nanozinc dispersion.

The cosmetic composition of the invention may also comprise, either in the aqueous spheroids or in the anhydrous continuous phase, or in both, at least one fragrance.

The cosmetic composition may also comprise at least one cosmetically acceptable excipient chosen from fillers, rheology agents, pH regulators, antioxidants, preserving agents, hydrating agents, humectants, etc.

The solid cosmetic composition of the invention is advantageously in the form of a stick or a solid gel cast in a dish or a pot.

According to a second aspect, the invention is directed toward a process for preparing a solid cosmetic composition according to the invention, comprising the following steps:

a—preparation of a liquid anhydrous continuous-phase composition by mixing, with stirring, preferably at a temperature ranging from 50 to 110° C., at least one lipophilic structuring agent in at least one hydrocarbon-based oil and/or one silicone oil, b—preparation of a liquid spheroid composition by mixing, with stirring, preferably at a temperature ranging from 50 to 110° C., at least one hydrophilic gelling agent in water, and optionally in the presence of at least one glycol as defined according to the invention, c—slow injection, in the form of droplets, of the liquid spheroid composition obtained on conclusion of step b—in a mixer, which is preferably T- or cross-shaped, in which the liquid anhydrous continuous-phase composition obtained on conclusion of step a—circulates continuously, d—at the mixer outlet, recovery of the composition obtained on conclusion of step c—comprising aqueous spheroids dispersed and in suspension in the anhydrous continuous phase, and e—cooling to room temperature of the composition obtained on conclusion of step d—, to obtain a solid cosmetic composition according to the invention.

According to a preferred embodiment, step a—of preparing a liquid anhydrous continuous-phase composition is performed at a temperature ranging from 60 to 110° C., advantageously from 70 to 110° C., and even more advantageously from 80 to 110° C.

Similarly, step b—of preparing a liquid spheroid composition is performed at a temperature ranging from 60 to 110° C., advantageously from 70 to 110° C., and even more advantageously from 80 to 110° C.

According to another preferred embodiment, the injection step c—is controlled to form droplets with a diameter ranging from 0.05 to 10.0 mm, preferably from 0.1 to 3.0 mm, and more preferentially from 0.5 to 2.5 mm.

According to another preferred embodiment, the injection step c—is performed in a T-shaped mixer which may be positioned:

either horizontally, the liquid spheroid composition being injected perpendicular to the liquid anhydrous continuous-phase composition, or vertically, the liquid spheroid composition and the liquid anhydrous continuous-phase composition being injected in a co-current position.

According to particularly preferred embodiment, the injection step c—is performed in a T-shaped mixer positioned horizontally. This position is preferred since it allows more regular injection of the droplets of liquid spheroid composition and better repeatability of the spheroid size.

The third subject of the invention is directed toward the use of a solid cosmetic composition according to the invention for making up and/or caring for bodily and/or facial skin, and notably the lips.

The invention is also directed toward a stick comprising a solid cosmetic composition according to the invention. More particularly, the invention is directed toward a lipstick, a foundation or an antisun stick, comprising a solid cosmetic composition according to the invention.

Lastly, a final subject of the invention relates to a process for making up and/or caring for bodily and/or facial skin, and notably the lips, comprising the following steps:

a'—uptake of an amount of solid cosmetic composition according to the invention, in an amount necessary to make at least one application, and b'—application of the solid cosmetic composition taken up during step a'—to the bodily and/or facial skin, and notably the lips.

Besides the preceding arrangements, the invention also comprises other arrangements which will emerge from the remainder of the description that follows, which relates to the preparation of cosmetic compositions according to the invention.

EXAMPLES

Example 1: Lipstick According to the Invention

An aqueous spheroid composition (composition A) corresponding to the formula presented in Table 1 below was prepared.

TABLE 1

| Chemical name | Commercial name | % by weight |
|---|---|---|
| | Water | 74.3 |
| | Vegetable glycerol (Cremer) | 10.0 |
| Agar-agar | Ina agar CS 83 (Iwase Cosfa) | 1.4 |
| Xanthan gum | Keltrol CG LAXT (Azelis) | 0.2 |
| Gellan gum | Kelcogel ® CG-LA (Azelis) | 0.2 |
| | Pigment | 13.2 |
| | Preserving agent | 0.7 |
| | TOTAL | 100.0 |

All the ingredients of composition A were heated, mixed and homogenized at a temperature of 85° C.

Characterization of the Aqueous Spheroids:

Measurement of the Hardness:

A 15 mL pill bottle was left at room temperature for 24 hours, and then placed in an oven at 20° C. for 24 hours.

The hardness measurements were performed using a texturometer (TA-XTPLUS texture analyzer, Stable Microsystems) according to the following parameters:

penetration speed: 1 mm·s$^{-1}$, cylindrical spindle used: cylinder 5 mm in diameter, penetration depth: 10 mm.

Three pill bottles were prepared for the aqueous spheroid composition and three measurements were taken per pill bottle, i.e. nine measurements in total for the aqueous spheroid composition.

The aqueous spheroid composition has a mean compression strength equal to 110 g after penetration of a cylindrical spindle 5 mm in diameter into said anhydrous continuous phase to a depth of 10 mm at a speed of 1 mm·s$^{-1}$, the measurement being performed at 20° C.

An anhydrous continuous-phase composition (composition B) corresponding to the formula presented in Table 2 below was prepared.

TABLE 2

| Chemical name | Commercial name | % by weight |
|---|---|---|
| Dibutyl lauroyl glutamide | AJK-OD2046 (Ajinomoto Health & Nutrition) | 20.0 |
| Polyamide-8 | SP OleoCraft ™ LP20 (Croda) | 20.0 |
| Octyldodecanol | Isofol ® 20 (Sasol) | 30.0 |
| Isononyl isononanoate | DUB ININ B (Stéarinerie Dubois) | 30.0 |
| | TOTAL | 100.0 |

Characterization of the Solid Anhydrous Continuous Phase:

The solid anhydrous continuous phase was characterized by measuring the hardness, by visual observation, and by evaluation of the sensory qualities.

To do this, all the ingredients of composition B were heated, with stirring, to a temperature of 85° C., and the mixture was poured into a 15 mL pill bottle and into a stick 1 cm in diameter.

Measurement of the Hardness:

The hardness was determined according to the same protocol as described above for the aqueous spheroids. The anhydrous continuous phase has a mean compression strength equal to 479 g after penetration of a cylindrical spindle 5 mm in diameter into said anhydrous continuous phase to a depth of 10 mm at a speed of 1 mm·s$^{-1}$, the measurement being performed at 20° C. It is thus considered as being "solid" for the purposes of the invention.

Visual Observation of the Stick:

The stick 1 cm in diameter was left at room temperature for 24 hours.

The stick was then opened over a length of 2.5 cm, and then held horizontally for a time of 1 minute. The curvature of the stick in the horizontal position was observed: it has a curvature in the continuity of the mechanism of the stick in the horizontal position, which confirms its "solid" nature for the purposes of the invention.

Evaluation of the Sensory Qualities of the Anhydrous Continuous Phase:

After 24 hours at room temperature, the stick is worn down perfectly and has good cohesion during spreading (does not break during application).

Preparation of the Lipstick According to the Invention:

The homogeneous, fluid mixture of composition A was injected in the form of droplets into a T-shaped mixer in which the anhydrous continuous phase of composition B circulates continuously in the liquid state, heated to a temperature of 90° C.

Characteristics of the Process:

Flow rate of composition A: 1 mL·min$^{-1}$,
Flow rate of composition B: 9 mL·min$^{-1}$,
Composition A/composition B weight ratio: 30/70,
Droplet diameter: 1.2 mm.

The composition obtained consisting of the anhydrous continuous composition of composition A and of the aqueous spheroids of composition B was poured, directly on exiting the process, into a packaging stick. The stick was then placed at room temperature for solidification.

A lipstick comprising aqueous spheroids dispersed in an anhydrous continuous phase was obtained. This product combines a freshness effect, very good nutrition and very good persistence of the color on the lips.

Example 2: Lipstick According to the Invention

An aqueous spheroid composition (composition A) corresponding to the formula presented in Table 3 below was prepared.

TABLE 3

| Chemical name | Commercial name | % by weight |
|---|---|---|
| | Water | 75.3 |
| | Vegetable glycerol (Cremer) | 10.0 |
| Agar-agar | Ina agar CS 83 (Iwase Cosfa) | 0.8 |
| | Pigment | 13.2 |
| | Preserving agent | 0.7 |
| | TOTAL | 100.0 |

All the ingredients of composition A were heated, mixed and homogenized at a temperature of 85° C.

Characterization of the Aqueous Spheroids:
Measurement of the Hardness:

The hardness was determined according to the same protocol as described in Example 1.

The aqueous spheroid composition has a mean compression strength equal to 115 g after penetration of a cylindrical spindle 5 mm in diameter into said anhydrous continuous phase to a depth of 10 mm at a speed of 1 mm·s$^{-1}$, the measurement being performed at 20° C.

An anhydrous continuous-phase composition (composition B) corresponding to the formula presented in Table 4 below was prepared.

TABLE 4

| Chemical name | Commercial name | % by weight |
|---|---|---|
| Polyethylene wax | Lipwax A-4 (Ina Trading) | 12.0 |
| Polyethylene | Jeenate ® 3H (Jeen International Corporation) | 3.2 |
| Cera alba | Cerabeil Blanchie DAB (Baerlocher) | 2.7 |
| C10-30 Cholesterol/ lanosterol esters | Super Sterol Ester ™ (Croda) | 5.6 |
| Hydrogenated polydecene | Dekanex 2006 FG (IMCD France) | 32.35 |
| Polyglyceryl-2 triisostearate | Polyglyceryl-2 Triisostearate MB | 32.35 |
| Calcium aluminum borosilicate | Ronaflake 17749 (Merck) | 11.8 |
| | TOTAL | 100.0 |

The ingredients were then all heated, with stirring, to a temperature of 85° C. After homogenization of the mixture, a solid gel was obtained.

Characterization of the Solid Anhydrous Continuous Phase:
Measurement of the Hardness:

The hardness was determined according to the same protocol as described in Example 1.

The solid anhydrous continuous phase has a mean compression strength equal to 2210 g after penetration of a cylindrical spindle 5 mm in diameter into said anhydrous continuous phase to a depth of 10 mm at a speed of 1 mm·s$^{-1}$, the measurement being performed at 20° C.

Visual Observation of the Stick:

The stick 1 cm in diameter was left at room temperature for 24 hours.

The stick was then opened over a length of 2.5 cm, and then held horizontally for a time of 1 minute. The curvature of the stick in the horizontal position was observed: it has a curvature in the continuity of the mechanism of the stick in the horizontal position, which confirms its "solid" nature for the purposes of the invention.

Evaluation of the Sensory Qualities of the Anhydrous Continuous Phase:

After 24 hours at room temperature, the stick is worn down perfectly and has good cohesion during spreading (does not break during application).

Preparation of the Lipstick According to the Invention:

The homogeneous, fluid mixture of composition A was injected in the form of droplets into a T-shaped mixer in which the anhydrous continuous phase of composition B circulates continuously in the liquid state, heated to a temperature of 90° C.

Characteristics of the Process:

Flow rate of composition A: 1 mL·min$^{-1}$,
Flow rate of composition B: 9 mL·min$^{-1}$,
Composition A/composition B weight ratio: 30/70,
Droplet diameter: 1.2 mm.

The composition obtained consisting of the anhydrous continuous composition of composition A and of the aqueous spheroids of composition B was poured, directly on exiting the process, into a packaging stick. The stick was then placed at room temperature for solidification.

A lip balm comprising aqueous spheroids dispersed in an anhydrous continuous phase was obtained. This product combines a freshness effect and very good nutrition of the lips.

The invention claimed is:

1. A solid cosmetic composition, characterized in that it comprises:
    aqueous spheroids comprising at least one hydrophilic gelling agent and water, said spheroids being dispersed in
    a solid anhydrous continuous phase comprising (a) at least one hydrocarbon-based oil and/or at least one silicone oil and (b) at least one lipophilic structuring agent,
wherein the aqueous spheroids are free of any outer coating and have a diameter of from 0.5 to 10.0 mm,
wherein the hydrophilic gelling agent in the aqueous spheroids is chosen from natural or synthetic polysaccharides and represents at least 0.3% by weight relative to the weight of the aqueous spheroids,
wherein the solid anhydrous continuous phase has a dropping point of greater than 50° C.,
wherein the hydrocarbon-based oil and/or at least one silicone oil represent from 20 to 80% by weight, relative to the total weight of the anhydrous continuous phase,
wherein the lipophilic structuring agent represents from 5 to 60% by weight, relative to the total weight of the anhydrous continuous phase, and
wherein the lipophilic structuring agent is at least one lipophilic gelling agent chosen from the group consisting of clays, optionally modified hectorites, dextrin palmitate, dextrin myristate, polyamides or silicone polyamides, L-glutamic acid or aspartic acid amides, hydroxystearic acid, and hydrocarbon-based block copolymers comprising at least one styrene unit.

2. The solid cosmetic composition as claimed in claim 1, in which the aqueous spheroids have a hardness defined by a compression strength of greater than or equal to 20 g at 20° C., after penetration of a cylindrical spindle 5 mm in diameter into said phase to a depth of 10 mm at a speed of 1 mm·s$^{-1}$.

3. The solid cosmetic composition as claimed in claim 1, in which the anhydrous continuous phase has a hardness defined by a compression strength of greater than or equal to 50 g at 20° C., after penetration of a cylindrical spindle 5 mm in diameter into said phase to a depth of 10 mm at a speed of 1 mm·s$^{-1}$.

4. The solid cosmetic composition as claimed in claim 1, in which the aqueous spheroids and the anhydrous continuous phase are immiscible at a temperature of greater than or equal to 40° C.

5. The solid cosmetic composition as claimed in claim 1, characterized in that it is free of surfactant.

6. The solid cosmetic composition as claimed in claim 1, in which the lipophilic structuring agent represents from 5% to 30% by weight relative to the total weight of the solid cosmetic composition.

7. The solid cosmetic composition as claimed in claim 1, in which the lipophilic structuring agent further comprises at least one additional lipophilic structuring agent chosen from the group consisting of waxes, butters, and pasty fatty compounds.

8. The solid cosmetic composition as claimed in claim 7, in which the waxes are chosen from natural waxes, hydrocarbon-based waxes, fatty alcohol waxes comprising from 20 to 60 carbon atoms, the hydrocarbon waxes comprising from 18 to 60 carbon atoms, and mixtures thereof.

9. The solid cosmetic composition as claimed in claim 7, in which the butters are chosen from C10-18 triglycerides (INCI name: C10-18 Triglycerides) including at room temperature and at atmospheric pressure a liquid fraction and a solid fraction, shea butter, Karité nilotica (*Butyrospermum parkii*) butter, galam (*Butyrospermum parkii*) butter, Borneo butter or grease or tengkawang (*Shorea stenoptera*) tallow, shorea butter, illipé butter, madhuca or *Bassia madhuca longifolia* butter, mowrah (*Madhuca latifolia*) butter, katiau (*Madhuca mottleyana*) butter, phulwara (*M. butyracea*) butter, mango (*Mangifera indica*) butter, murumuru (*Astrocatyum murumuru*) butter, kokum (*Garcinia indica*) butter, ucuuba (*Virola sebifera*) butter, tucuma butter, painya (Kpangnan) (*Pentadesma butyracea*) butter, coffee (*Coffea arabica*) butter, apricot (*Prunus armeniaca*) butter, macadamia (*Macadamia temifolia*) butter, grape (*Vitis vinifera*) seed butter, avocado (*Persea gratissima*) butter, olive (*Olea europaea*) butter, sweet almond (*Prunus amygdalus dulcis*) butter, cocoa (*Theobroma cacao*) butter, sunflower butter, the butter under the INCI name *Astrocaryum murumuru* Seed Butter, the butter under the INCI name *Theobroma grandiflorum* Seed Butter, the butter under the INCI name *Irvingia gabonensis* Kernel Butter, jojoba esters (mixture of hydrogenated jojoba wax and oil) (INCI name: Jojoba Esters), ethyl esters of shea butter (INCI name: Shea butter ethyl esters), and mixtures thereof.

10. The solid cosmetic composition as claimed in claim 7, in which the pasty fatty compounds are chosen from the group consisting of lanolin and derivatives thereof, polymeric silicone compounds, copolymers of alkyl (meth) acrylates, homopolymer and copolymer oligomers of vinyl esters containing C8-C30 alkyl groups, homopolymer and copolymer oligomers of vinyl ethers containing C8-C30 alkyl groups, liposoluble polyethers resulting from polyetherification between one or more C2-C50 diols, copolymers of ethylene oxide and/or of propylene oxide with C6-C30 long-chain alkylene oxides, diglycerol esters, arachidyl propionate, phytosterol esters, noncrosslinked polyesters resulting from polycondensation between a linear or branched C4-C50 dicarboxylic or polycarboxylic acid and a diol or a polyol, the ester resulting from the esterification reaction of hydrogenated castor oil with isostearic acid, a mixture of soybean sterols and of oxyethylenated (5 OE) oxypropylenated (5 OP) pentaerythritol, and mixtures thereof.

11. The solid cosmetic composition as claimed in claim 1, in which the lipophilic gelling agents are chosen from the group consisting of optionally modified hectorites, dextrin palmitate, dextrin myristate, polyamides or silicone polyamides, L-glutamic acid or aspartic acid amides, and hydrocarbon-based block copolymers comprising at least one styrene unit.

12. The solid cosmetic composition as claimed in claim 1, in which the aqueous spheroids comprise at least one glycol.

13. The solid cosmetic composition as claimed in claim 1, in which the aqueous spheroids and/or the anhydrous continuous phase comprise at least one pigment and/or at least one nacre.

14. The solid cosmetic composition as claimed in claim 1, in which the aqueous spheroids and/or the anhydrous continuous phase comprise at least one UV-screening agent.

15. The solid cosmetic composition as claimed in claim 14, in which the UV-screening agent is chosen from the group consisting of benzophenone-3, benzophenone-4, ethylhexyl salicylate, octocrylene, octyl methoxycinnamate, homosalate, polysilicone-15, diethylamino hydroxybenzoyl hexyl benzoate, bis-ethylhexyloxyphenol methoxyphenyl triazine, titanium oxide or zinc oxide pigments, phenylbenzimidazolesulfonic acid, a nanotitanium or nanozinc dispersion, and mixtures thereof.

16. The solid cosmetic composition as claimed in claim 1, in which the spheroids and/or the anhydrous continuous phase comprise at least one fragrance.

17. The solid cosmetic composition as claimed in claim 1, in which the spheroids represent from 10% to 80% by weight relative to the total weight of the solid cosmetic composition.

18. A process for preparing a solid cosmetic composition as claimed in claim 1, comprising:
   a—preparation of a liquid anhydrous continuous-phase composition by mixing, with stirring at least one lipophilic structuring agent in a hydrocarbon-based oil and/or a silicone oil,
   b—preparation of a liquid spheroid composition by mixing, with stirring at least one hydrophilic gelling agent in water,
   c—slow injection, in the form of droplets, of the liquid spheroid composition obtained on conclusion of step b—in a mixer in which the liquid anhydrous continuous-phase composition obtained on conclusion of step a—circulates continuously,
   d—at the mixer outlet, recovery of the composition obtained on conclusion of step c—comprising aqueous spheroids dispersed and in suspension in the anhydrous continuous phase, and
   e—cooling to room temperature of the composition obtained on conclusion of step d—, to obtain a solid cosmetic composition as claimed in claim 1.

19. A stick, comprising a solid cosmetic composition as claimed in claim 1.

20. A solid gel cast in a dish or a pot, comprising a solid cosmetic composition as claimed in claim 1.

21. A lipstick, comprising a solid cosmetic composition as claimed in claim 1.

22. A foundation, comprising a solid cosmetic composition as claimed in claim 1.

23. An antisun stick, comprising a solid cosmetic composition as claimed in claim 1.

24. A process for making up and/or caring for bodily and/or facial skin, comprising:
   a'—uptake of an amount of solid cosmetic composition as claimed in claim 1, in an amount necessary to make at least one application, and
   b'—application of the solid cosmetic composition taken up during step a'—to the bodily and/or facial skin.

25. The process as claimed in claim 24, wherein the solid cosmetic composition is applied to lips.

* * * * *